United States Patent [19]
Bourdeau et al.

[11] 3,960,666
[45] June 1, 1976

[54] PREPARATION OF AN ENZYME-CELLULOSE COMPLEX

[75] Inventors: Jean Paul Bourdeau; Jean Louis Seris, both of Pau; Rene Pornin, Arthez-de-Bearn, all of France

[73] Assignee: Societe Nationale des Petroles d'Aquitaine, Paris, France

[22] Filed: Oct. 8, 1974

[21] Appl. No.: 513,048

[30] Foreign Application Priority Data
Oct. 12, 1973  France .............................. 73.36428

[52] U.S. Cl. .................................. 195/68; 195/63; 195/DIG. 11; 426/36
[51] Int. Cl.² ..................... A23C 19/02; C07G 7/02
[58] Field of Search ................ 195/63, 68, DIG. 11; 426/36

[56] References Cited
UNITED STATES PATENTS
3,841,969  10/1974  Emery et al. .......................... 195/63

OTHER PUBLICATIONS
Zaborsky, O., Immobilized Enzymes, CRC Press, Cleveland, Ohio, May 1973 (pp. 28 and 35)

Weliky et al., The Chemistry and Use of Cellulose Derivatives for the Study of Biological Systems, Immunochemistry, vol. 2, 1965 (pp. 293–303).

*Primary Examiner*—David M. Naff
*Attorney, Agent, or Firm*—Ostrolenk, Faber, Gerb & Soffen

[57] ABSTRACT

Enzymes are fixed to cellulose containing 5 to 25% lignin to form an enzyme-cellulose complex by a process involving treating cellulose pieces with an alkaline solution to remove lignin on the surface of the pieces, treating the resultant cellulose pieces with a sulfochlorinating or a chlorinating agent in an excess of pyridine until sulfur and/or chlorine is combined with the cellulose, washing the sulfur and/or chlorine-containing cellulose pieces and treating the pieces with an aqueous enzyme solution to attach enzymes thereto. A very important application is preparation of a rennet-cellulose complex and using the complex for coagulating milk in making cheese.

5 Claims, 1 Drawing Figure

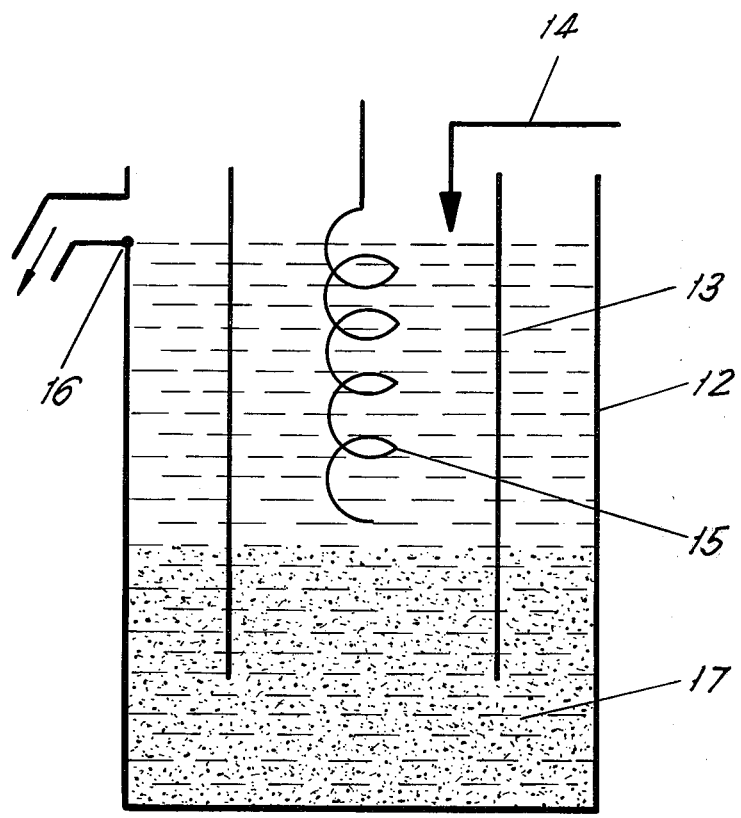

PREPARATION OF AN ENZYME-CELLULOSE COMPLEX

DESCRIPTION OF THE INVENTION

The invention relates to a new enzyme complex, in which this latter is fixed in a stable manner on a solid support, more especially on a cellulose material. It is concerned with the enzymes thus supported and with a process for the preparation thereof.

The fixation of enzymes on solid supports has formed the subject of research during the last decade, with a view to making possible the achievement of enzymatic reactions in heterogeneous medium. It would in effect be of interest to be able to recover the enzyme when its participation in a reaction is terminated. On the one hand, the purity of the finished product would be better if the enzyme did not remain in the reaction medium, as is generallly the case; on the other hand, the operation would be more economical, especially as regards fairly expensive enzymes. This problem is particularly important as regards the rennet which is becoming increasingly less available at the present time, although the need for this substance, namely, in the manufacture of cheeses, increases every day. Attemps have also been made to fix enzymes on solid supports, particularly agarose and cellulose, for using it in continuous systems; nevertheless, these efforts have not given the expected results; even after activation of the support by agents such as cyanogen halides, glutaraldehyde, etc., the complexes with the enzymes did not show the necessary stability. Thus, GREEN and CRUTCHFIELD (Biochem. Journ. 1969, pages 183–190), who have worked on this problem and tested the coagulation of milk in the presence of rennet fixed on activated pure cellulose, reached the conclusion that these efforts were a failure from the industrial point of view.

The present invention resolves this problem and permits complexes of enzymes fixed on cellulose materials to be obtained, these complexes having an excellent stability, that is to say, the enzyme is practically not dissolved in the reaction medium, remains solidly attached to its support and can thus be used again numerous times. The new complexes of supported enzyme in addition present the advantage of being used in much larger grains than that which was possible according to the prior art; the result thereof is the possibility of using them just as well in the form of fixed beds as mobile beds, in an enzymatic treatment in liquid medium. In the very important particular application to the coagulation of milk, the new complexes according to the invention permit a considerable economy to be made as regards rennet and cheeses to be obtained which are free from this latter.

The present invention arises from the unexpected discovery that celluloses which contain a certain proportion of lignin constitute enzyme supports which are much better than the pure cellulose. In the past, it was always sought to prepare a cellulose as pure as possible for serving as a support for enzymes, because it was assumed on principle that the presence of lignin and other vegetable substances capable of accompanying the cellulose prevented the fixation of enzymes; this is true in that a too strong proportion of lignin is prejudicial to such a fixation; the unexpected element of the present invention consists just in the fact that, if too much lignin is is harmful, a proportion which is contained within certain limits is on the contrary very favourable, provided that, in the structure of the selected cellulose, the lignin be dispersed in the cellulosic mass and not only concentrated at the surface of the latter, thus assuring the cohesion of the grains or fibers.

The new complex of enzyme fixed on the cellulose according to the invention is characterized in that the cellulose support contains 5 to 25 percent of lignin by weight of the dry material, this proportion being preferably from 10 to 20 percent, the lignin being dispersed substantially uniformity throughout the cellulose.

The cellulose with a moderate lignin content, which is suitable according to the present invention, can be derived from any one of the well known natual sources, as for examle wood, of which it is possible to use the waste material, especially chips or sawdust, shavings or the like paper pulp can likewise be used, provided that it has a lignin content which is within the aforementioned limits. One special source very highly recommended for the quality of the cellulose as regards the retention of enzymes, is the stalks of cereals and particularly maize cobs.

The lignified cellulose, which is utilised in the present invention, can be provided in the form of pieces or particles of very variable dimensions, which extend for example from 0.2 mm up to several cms, depending on its origin and the form of the apparatus in which it has to be used; in general, the most practical dimensions are from about 0.3 to 10 mm or better still from 0.5 to 5 mm. With such dimensions, the result is that there are obtained contact surfaces which are adequate for providing a very efficient activity of the cellulose-enzyme complex, whereas according to the prior art, that is to say, with pure cellulose, it was scarcely possible to use fibres having a diameter exceeding 0.05 mm, which naturally did not permit the use of a fixed bed capable of supporting a strong rate of flow without clogging and involving a prohibitive pressure drop.

Just as for pure cellulose, there is great advantage in activating the lignified cellulose before fixing the enzyme thereon; the appropriate activation leads to extremely stable complexes. The different known activation treatments, such as polydiazotisation, aminobenzylation, bromoacetylation, treatment with cyanogen bromide or with glutaraldehyde, etc., can thus be applied, just as with pure cellulose; however, remarkable results are obtained if, before coupling with the enzyme, the lignified cellulose is treated with a chlorinating or sulfochlorinating agent, as for example sulphuryl chloride, thionyl chloride, phosphorus trichloride or pentachloride or similar agent. Particularly stable and efficient complexes are obtained with lignified celluloses which have undergone such a treatment in the presence of pyridine. The activation of the cellulose selected according to the present invention can be carried out according to the working procedures indicated in Examples I to V of French Pat. application No. 72 40492 (publication Ser. No. 2,206,329 of June 7,1974). As regards the coupling of the enzymes with the activated cellulose, it can be effected according to Examples VI to IX of the same publication.

One cellulose which leads to particularly advantageous results is the cellulose of maize cobs in pieces from 0.5 to 10 mm, activated beforehand by the action of thionyl chloride in the presence of an excess of pyridine, so that the final product contains about 2 to 6 percent of sulphur and preferably 3 to 4 percent, the content of fixed chlorine always being less than that of the sulphur; preferably the percentage of chlorine is less than 1 percent, and it may be 0.

The new cellulose support according to the invention, as well as the process for obtaining enzyme-cellulose complexes, which is connected therewith, are applicable to a large number of enzymes belonging to different classes; thus, it is possible, for example, to fix the enzymes such as chymotrypsin, trypsin, lysosime, rennet, invertase, amylase, maltase, β-galactosidase, pectinases, various other hydrolases, especially phosphatases, ribonucleases, etc.

The process according to the invention for the preparation of the new enzyme/cellulose complexes consists in comminuting a cellulose, containing the adequate proportion of lignin, into pieces or particles of the size as indicated above and in treating these latter first of all with an alkaline solution having a normality of about 3 to 6, preferably about 4.5, so as to dissolve the fraction of lignin which finds at the surface of the grains. This treatment is preferably carried out at normal temperature for 10 to 30 minutes. The cellulose grains are then separated from the liquid and thoroughly washed with cold water until the filtrate is no longer coloured. They are then dehydrated by means of an alcohol and then washes with puridine. $SOCl_2$, or possibly another chlorinating agent, is progressively caused to enter a suspension of these grains in pyridine, while regulating the temperature to less than 60°C and preferably to or in the region of 55°C. The control of the temperature has an influence on obtaining a support containing the aforementioned optimal contents of S and Cl; in time, the S/Cl ratio develops as shown by the graph in the above mentioned French Pat. application No. 72 40 492. After standing for a time of about one hour, the reaction is stopped by cooling, for example, by introducing the reaction mixture into an iced water bath. The grains of cellulose thus treated are separated and carefully washed with water and then with an acid solution having pH in the region of 2, until the pyridine is completely eliminated. Finally, the grains are washed with an alcohol and dried at moderate temperature, preferably below 50°C.

The coupling of the desired enzyme with the grains thus prepared takes place in an aqueous buffering solution the pH of which is adapted to the particular enzyme. For example, for rennet, it is advantageous to use a buffering solution of phosphates with a preferred pH value from 5.9 to 6.4. The medium is agitated at a moderate temperature, which is generally between ambient temperature and 50°C, for the time which is necessary for fixing the enzyme, this generally being of the order of 24 hours.

After separation of the grains thus coupled with the enzyme, it is preferred to carry out the elimination of the enzyme portion which is not fixed by covalence; this can be effected by washing with buffering solutions of suitable pH value and with water. It is advisable to preserve the grains obtained at a relatively low temperature in a pH buffering solution in which the enzyme is particularly stable.

The following non-limiting example illustrates the application of the invention to the very important industrial case of rennet.

EXAMPLE 1

Maize cobs, containing about 80 percent of cellulose and 15 percent of lignin, are reduced into grains of 1.5 to 2.5 mm.

50 g of these grains are placed in 18 percent sodium hydroxide solution and this is stirred for 15 minutes at normal temperature. The grains are then separated and thoroughly washed with cold water, until the filtration has only a slight coloration. The washing is completed with 1 liter of methanol and then with 400 ml of pyridine.

The grains are then poured into 800 ml of pyridine, after which 100 ml of $SOCl_2$ are added dropwise to the agitated pyridine during 45 minutes. The temperature of the reaction mixture is raised up to 55°C and the medium suddenly becomes intensively coloured.

1 hour after completing the introduction of the thionyl chloride, the mixture is poured into ice containing water, and the grains are then separated and washed with several liters of water and then with an HCl solution of pH 2, until there is complete elimination of the pyridine adsorbed on the grains. The washing is completed with 1 liter of methanol. The grains thus obtained are dried at 40°C.

It is found that the cellulose treated contains about 3.5 percent of sulphur and only traces of chlorine.

Into 160 ml of a buffering solution of phosphates of pH 6.2 are introduced 16 g of the grains prepared as indicated above and 40 ml of rennet which is known commercially under the trade mark CARLIN. The whole is maintained at 40°C under stirring for 24 hours.

The grains are then separated and there is carried out the desorption of the rennet which is not chemically fixed, by washing: first of all with 250 ml of the same buffering solution as above, then with 2 liters of distilled water and finally with 250 ml of acetate buffering solution of pH 4.4. The mother solutions from these treatments are used again. The grains thus obtained of the complex consisting of rennet and maize cob cellulose are kept at 4°C in 250 ml of acetate buffering solution.

EXAMPLE 2

Grains of the cellulose-rennet complex, prepared following the procedure of Example 1, were used for curdling milk in an experimental production of cheese. The curdling was operated in continue in an equipment diagramatically shown on the appended drawing.

The equipment comprises a cylindrical vertical vat 12, containing a coaxial sleeve 13 open at its two ends, within which is lodged a stirrer 15. Through conduit 14 milk is continuously poured into the sleeve 13. The grains 17 of cellulose-rennet complex are placed within the lower part of the vat and sleeve, and they are constantly kept in suspension in the milk, within sleeve 13, by the action of the stirrer 15. While the milk, after contact with the complex, leaves the vat through overflow 16, the grains tend to settle in the annular space between the walls of 12 and 13; thus the milk continuously flows out and the grains remain within the vat. The milk, so pretreated with the enzyme solid complex, is then passed in a usual heated container (non represented on the drawing) where it is curdled by mer heating.

8 grams of cellulose were used, on which 0.04 grams of commercial rennet were fixed as described in Example 1. Milk was passed through the apparatus at a rate of 0.63 liter per hour, and its temperature was 15°C. The region 17 of the suspension of grains extended approximately over one-third of the height of vat 12; at this level the degree of caseine proteolysis reached about 80 percent, while this degree was about 100 percent in the milk leaving the vat by the overflow 16.

The milk was then heated to 37°C and thereby rapidly curdled in the above mentioned usual container into which it flowed from 16. In this way 35 liters of milk were treated in 55 ½ hours with the single charge of 8 g of cellulose complex containing only 0.04 g of rennet.

When the usual method of curdling milk by directly adding rennet is carried out, the amount of 0.04 g of the enzyme can make curdle only 0.4 liters of milk. That means the complex according to the invention leads to a 87 times greater efficiency of the enzyme, as it permits of treating 35 liters instead of 0.4.

Comparative experiences with known pure celluloserennet complexes were not successful because these can be obtained only in the form of so fine fibres (less than 0.05 mm) that neither fixed nor fluidized beds of them could correctly work.

EXAMPLE 3

The preparation of Example 1 was repeated, but the 100 ml of thionyl chloride $SOCl_2$ were replaced by 68 ml of sulfuryl chloride $SO_2Cl_2$, and this was allowed to react during 2 hours. The cellulose obtained contained 3.1% of sulfur and 0.3% Cl. It gave with enzymes complexes which showed an efficiency similar to that of Examples 1 and 2.

EXAMPLE 4

The procedure of Example 1 is repeated except that the thionyl chloride is replaced by 77 ml of phosphorous trichloride and the mixture is kept at 5°C for one hour. The activated cellulose obtained contains 1.85% Cl. When trypsine is fixed thereon, the complex obtained has substantially the same activity as trypsine itself, but it may be used in a great number of runs as, being insoluble in the reaction medium (for examle in albumen proteolysis), it does not get lost as soluble trypsine does.

EXAMPLE 5

In the procedure of Example 1 wood sawdust having 22 percent of lignin is substituted for the maize cobs and the thiochlorination lasts 4 hours, while temperature is kept between 25° and 32°C. The activated cellulose obtained contains 5.6 percent of sulfur and 3.2 percent of chlorine; it easily fixes rennet, chymotrypsine, betagaelactosidase, amylase and maltase. The cellulose-enzyme complexes keeps longtime their enzyme and are usable many times for enzymatic hydrolysis runs, for instance with starch or proteines.

EXAMPLE 6

13 grams of the activated cellulose according to Example 1 are mixed with 40 ml of aqueous solution of 1,800 units β-galactosidase and 100 ml of a potassium phosphate buffer of pH 7.2. The mixture is stirred during 48 hours at 40°C. Then the grains of cellulose are separated from the liquid by filtration, and washed. They are found to be constituted by a complex cellulose-β-galactosidase having 1,000 units of this enzyme. This activity is determined by the known method O.N.P.G. (hydrolysis of o-nitrophenyl-β-D-galactopyranoside). The solid complex is kept in a phosphate buffer of pH 6.2.

The invention claimed is:

1. The method of producing an enzymatic solid composition consisting of cellulose pieces having fixed thereto an enzyme, which comprises: (a) comminuting a cellulose material having 5 to 25 percent by weight of lignin, with respect to dry cellulose, into pieces having dimensions of about 0.2 to about 10 mm; (b) treating the pieces with an alkaline aqueous solution until the surface of the pieces is substantially free of lignin; (c) washing the treated pieces with water; (d) introducing the pieces into an excess of pyridine, adding a chlorinating agent from the group consisting of thionyl chloride, sulfuryl chloride, phosphorus trichloride and phosphorus pentachloride, to the pyridine, and allowing the mixture to stand until a proportion of sulfur of 0 to 6 percent of dry cellulose and a proportion of chlorine of 0 to 3.2 percent of dry cellulose is combined with the cellulose, at least one of the two proportions being more than 0; (e) separating the pieces from the pyridine and the chlorination agent, washing them with water and with an acid, and then introducing them into an aqueous buffer solution having a pH at which the given enzyme is not stable; (f) mixing the buffer solutions with enzyme and stirring the mixture until enzyme is bound to said pieces, and (g) separating the pieces from the solution and washing them.

2. Method according to claim 1, wherein said cellulose material is constituted by maize cobs.

3. Method according to claim 2, wherein the chlorination agent is thionyl chloride and the enzyme is rennet.

4. Method according to claim 1, wherein the temperature of the mixture of cellulose, pyridine and chlorinating agent is kept at 5° to 60°C.

5. Method according to claim 3, wherein the temperature of the mixture of cellulose, pyridine and thionyl chloride is kept at 25° to 55°C.

* * * * *

UNITED STATES PATENT OFFICE
CERTIFICATE OF CORRECTION

Patent No. 3,960,666  Dated June 1, 1976

Inventor(s) Jean Paul Bourdeau; Jean Louis Seris, Rene Pornin

It is certified that error appears in the above-identified patent and that said Letters Patent are hereby corrected as shown below:

Column 1, line 67, for "is is" read --is--.

Column 6, line 38, for "not stable" read --most stable--.

Signed and Sealed this

Nineteenth Day of October 1976

[SEAL]

Attest:

RUTH C. MASON
Attesting Officer

C. MARSHALL DANN
Commissioner of Patents and Trademarks